United States Patent [19]

Tomita et al.

[11] Patent Number: 4,477,682
[45] Date of Patent: Oct. 16, 1984

[54] PROCESS FOR PRODUCING 4-HYDROXY-2,4,6-TRIMETHYLCYCLOHEXA-2,5-DIENE-1-ONE

[75] Inventors: Tetsuo Tomita, Sakura; Masahiro Jono; Toshiaki Takata, both of Kanamachi, all of Japan

[73] Assignee: Mitsubishi Gas Chemical Company, Inc., Tokyo, Japan

[21] Appl. No.: 451,788

[22] Filed: Dec. 21, 1982

[30] Foreign Application Priority Data

Dec. 28, 1981 [JP] Japan ................................ 56-211901

[51] Int. Cl.³ ............................................. C07C 45/30
[52] U.S. Cl. .................................................... 568/362
[58] Field of Search ................... 568/362; 260/396 N, 260/347

[56] References Cited

U.S. PATENT DOCUMENTS 2,662,918 12/1953 Spaulding ............................ 568/362
3,631,185 12/1971 Laufer ................................ 568/347
3,895,069 7/1975 Halstead ............................. 568/362

OTHER PUBLICATIONS

Fieser et al., "Reagents for Organic Synthesis", pp. 487–489, (1976).

Primary Examiner—James H. Reamer
Attorney, Agent, or Firm—Frishauf, Holtz, Goodman & Woodward

[57] ABSTRACT

A process for the preparation of 4-hydroxy-2,4,6-trimethylcyclohexa-2,5-diene-1-one from 2,4,6-trimethylphenol is disclosed, comprising reacting 2,4,6-trimethylphenol with an aqueous solution or suspension of hypohalogenous acid or salt thereof in an aqueous medium or mixed medium of water and specific organic solvents. This process enables to prepare 4-hydroxy-2,4,6-trimethylcyclohexa-2,5-diene-1-one, which is a precursor for 2,3,5-trimethylhydroquinone, a starting material for the preparation of vitamin E, by a simplified operation, safely and at high yields.

35 Claims, No Drawings

PROCESS FOR PRODUCING 4-HYDROXY-2,4,6-TRIMETHYLCYCLOHEXA-2,5-DIENE-1-ONE

BACKGROUND OF THE INVENTION

The present invention relates to a novel process for producing 4-hydroxy-2,4,6-trimethylcyclohexa-2,5-diene-1-one, and more particularly, to a process for preparing 4-hydroxy-2,4,6-trimethylcyclohexa-2,5-diene-1-one from 2,4,6-trimethylphenol, and hypohalogenous acid or salt thereof.

4-Hydroxy-2,4,6-trimethylcyclohexa-2,5-diene-1-one (hereinafter referred to as "HTCD") is a compound represented by the following formula:

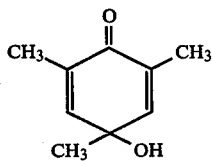

It has long been known that HTCD is converted into 2,3,5-trimethylhydroquinone on heating in the presence of alkalis. This 2,3,5-trimethylhydroquinone is a compound which has received increasing attention in recent years as a starting material for use in the preparation of vitamin E. It has thus bendesired to develop a method of preparing HTCD inexpensively.

Several methods are known for the synthesis of HTCD. Typical examples are:

(1) a method in which 2,4,6-trimethylphenol (hereinafter referred to as "TMP") is reacted with monopotassium persulfate (see Bamberger, Ber., 36, 2033);

(2) a method of oxidizing TMP with periodic acid; (see E. Adler et al., Acta. Chem. Scand., 29, 909 (1975))

(3) a method of electrolytic oxidation of TMP (see C. G. Beddows & D. V. Wilson, *J. C. S. (Perkin* 1), 2337 (1973)); and (4) a method of oxidizing TMP with molecular oxygen (see DT-OS 2,747,497 and Japanese patent application Laid-Open Nos. 121,252/1975, 127,937/1974).

These methods, however, are not desirable from an industrial or commercial standpoint. In the methods (1) and (2), specific and expensive oxidizing agents are used, and therefore they are disadvantageous from an economic standpoint. The method (3) is disadvantageous for its industrial practice because it needs a very specific reactor.

Of the above-described methods, the method (4) is considered to be an industrially most promising method.

For example, DT-OS 2,747,497 discloses a method in which TMP is reacted in the presence of isopropyl alcohol under an air pressure of 100 atmospheres by the use of a catalyst containing cobalt to prepare HTCD in the yield of 99%. In the commercial practice of this method, however, the danger of explosion is very large, because the contacting of high-pressure air with organic compounds often causes an explosion.

Japanese patent application Laid-Open No. 121252/1975 describes that when a solution of TMP dissolved in NaOH-containing water is repeatedly passed through a multi-stage reaction column charged with pure oxygen gas under a pressure of 70 kg/cm$^2$G by means of a pump, there is formed HTCD at the selectivity of 70%. In accordance with this method, there is no fear of explosion. However, in such a high-pressure oxygen gas atmosphere, substances are liable to become very inflammable, and there is a danger of even metals being set on fire. It is therefore very dangerous to allow a large amount of oxygen gas to stay in the reaction column. Thus, on the whole, it is not considered that the danger associated with the industrial practice is reduced.

In general, production costs of high-pressure reactors are high, obviously constituting a factor in increasing the costs of reaction products.

Japanese patent application Laid-Open No. 127937/1974 discloses a method of oxidizing TMP with oxygen under atmospheric pressure in the presence of a tetraphenylporphyrin cobalt complex catalyst. This method, however, is not industrially advantageous because the complex catalyst is very expensive.

As described above, the conventional methods suffer from industrial disadvantages and are not always sufficiently satisfactory.

SUMMARY OF THE INVENTION

An object of the invention is to provide a process for producing HTCD which is free from the above-described various industrial disadvantages. Another object of the invention is to provide a process for producing HTCD which is very safe and simplified in operation.

A further object of the invention is to provide a process for producing HTCD with high purity in high yield.

The present invention provides a process for producing 4-hydroxy-2,4,6-trimethylcyclohexa-2,5-diene-1-one (HTCD) which comprises reacting 2,4,6-trimethylphenol with hypohalogenous acid or salt thereof in an aqueous medium or a mixed medium of water and at least one organic solvent selected from the group consisting of nitriles having from 1 to 4 carbon atoms, carboxylic acid esters derived from carboxylic acids having from 1 to 6 carbon atoms and alcohols having from 1 to 6 carbon atoms, ethers having from 2 to 8 carbon atoms, nitro compounds having from 1 to 6 carbon atoms, amides having from 1 to 4 carbon atoms, nitrogen-containing heterocyclic compounds having from 4 to 7 carbon atoms, aliphatic hydrocarbons having from 5 to 10 carbon atoms, alicyclic hydrocarbons having from 5 to 10 carbon atoms, aromatic hydrocarbons having from 6 to 12 carbon atoms, halogenated hydrocarbons obtained by halogenation of the hydrocarbons, carbon disulfide, dimethylsulfoxide, aliphatic carbonic acid esters having from 3 to 7 carbon atoms, phosphoric acid esters having from 3 to 9 carbon atoms, and sulforane, wherein the weight ratio of water to 2,4,6-trimethylphenol being at least 10:1.

DETAILED DESCRIPTION OF THE INVENTION

The starting material, 2,4,6-trimethylphenol (hereinafter referred to as "TMP"), as used herein can be obtained by fractional distillation of tar, or be synthesized by organic reactions. In more detail, TMP can be produced by an alkali fusion process of mesitylenesulfonic acid, alkylation of phenols, oxidation of mesitylene, acid decomposition of 2,4,6-trimethylcumene hydroperoxide, and dehydrogenation or dehydration of alkylcyclohexane rings.

In general, hypohalogenous acid or salt thereof used herein is suitably added in the form of an aqueous solution. In the case of water-insoluble salts, however, they may be added in the form of aqueous suspension.

Hypohalogenous acid or salt thereof which can be used includes hypochlorous acid, hypobromous acid, sodium hypochlorite, potassium hypochlorite, magnesium hypochlorite, barium hypochlorite, calcium hypochlorite, bleaching powder, barium hypobromite, lithium hypochlorite, sodium hypobromite, calcium hypobromite, and lithium hypobromite. These acids or salts thereof may be used alone or in combination with each other. Moreover, they may contain inorganic salts other than the hypohalogenous acid salts. In fact, sodium hypochlorite which is industrially used contains some amount of sodium chloride, and with such industrial sodium hypochlorite the reaction of the invention proceeds satisfactorily. From an industrial viewpoint, sodium hypochlorite and bleaching powder are preferably used as hypohalogenous acid salts.

Since the reaction between TMP and hypohalogenous acid or salt thereof proceeds very rapidly, the concentration of hypohalogenous acid or salt thereof is a significant factor to control the reaction and to attain high yields. The concentration of hypohalogenous acid or salt thereof in its aqueous solution or suspension is usually from 0.01 to 50% by weight, preferably from 0.1 to 15% by weight, and more preferably from 0.2 to 10% by weight.

When TMP is dissolved in an organic solvent and is used to conduct the reaction, the concentration of hypohalogenous acid or salt thereof is particularly preferred to be from 0.5 to 8% by weight. In this specification, the word "the concentration of hypohalogenous acid or salt thereof" means the concentration of the acid or salt itself, and does not mean the concentration of effective halogen or activated halogen.

To prevent the secondary reaction between the hypohalogenous acid or salt thereof and the formed HTCD, it is preferred for the concentration of hypohalogengus acid or salt thereof in its aqueous solution or suspension to be as low as possible. In this case, however, a large amount of solvent is needed to extract HTCD. Thus it is industrially disadvantageous to use very low concentrations of hypohalogenous acid or salt thereof in the aqueous solution or suspensions.

Hypohalogenous acid or salt thereof is used in an amount of from 0.1 to 10 moles, preferably from 0.5 to 2 moles, and more preferably from 0.8 to 1.3 moles, per mole of TMP.

However, it is rather meaningless to strictly define the amount of hypohalogenous acid or salt thereof being used in relation to TMP. For example, when an aqueous solution of hypohalogenous acid or salt thereof is added dropwise to an aqueous medium or organic solvent-containing aqueous medium in which TMP is contained to react hypohalogenous acid or salt thereof with TMP, it is believed that the dynamic stoichiometric ratio is such that TMP is present excessively. In this case, the amount of hypohalogenous acid or salt thereof being used in relation to TMP should be defined as the total amount of hypohalogenous acid or salt thereof used based on the initially charged amount of TMP. The same is the case with the embodiment that the reaction is carried out while adding TMP-containing medium to an aqueous solution or suspension of hypohalogenous acid or salt thereof.

The general procedure in the process of the invention is to contact TMP with hypohalogenous acid or salt thereof in an aqueous medium or organic solvent-containing aqueous medium for a suitable period of time whereby the desired HTCD can be readily produced in high yields.

In the invention, the presence of the aqueous medium or organic solvent-containing aqueous medium is essential for the production of HTCD in high yields. If water is not present at all in the reaction system, or even though the reaction system contains water, there is not present a proper amount of water, the desired HTCD can be obtained only in seriously reduced yields although the reaction proceeds. This is not desirable for the industrial practice of the invention.

In connection with the amount of water added, it is necessary that the weight ratio of water (including both the water to be added and the water in which hypohalogeneous acid or salt thereof is dissolved or suspended) to TMP is at least 10:1, preferably at least 20:1, and more preferably at least 25:1.

TMP is insoluble or hardly soluble in water. In the reaction of the invention, TMP is not always required to be dissolved in the medium. When TMP is reacted in a suspension condition in aqueous medium, oily HTCD is formed, exerting no adverse effects on the reaction and allowing it to proceed very smoothly.

In one aspect of the invention, the present reaction can be carried out in a mixed medium of water and an organic solvent or solvents, i.e., so-called organic solvent-containing aqueous medium. These organic solvents are not always necessary to be thoroughly soluble in water, and are sufficient to be capable of dissolving TMP and HTCD. Since these organic solvents increase the solubilities of TMP and HTCD, both being insoluble in water, the use of the organic solvents in the industrial practice of the invention produces various advantages in that operations of handling solids, for example, in feeding the starting material, TMP, to the reaction system, and withdrawing therefrom the product, HTCD, or purification of HTCD, can be omitted, enabling to simplify the process of production very much, and that the reactivity between hypohalogenous acid or salt thereof and TMP, and the yield of HTCD can be greatly increased. However, the use of a large amount of organic solvent leads to increases in the loss of organic solvent and the quantity of energy consumed for the recovery thereof. This is disadvantageous in the industrial practice of the invention. Thus, in the industrial practice of the invention, it is necessary to appropriately determine the type and amount of the organic solvent taking into consideration the above-described circumstances.

In the invention, alcohols, ketones containing active hydrogen, strongly acidic carboxylic acids, and amines, which are generally widely used as organic solvents, are not suitable for use as the organic solvents in the process of the invention, because they seriously reduce the reactivity. However, the use of such organic solvents within the range of 20% by weight or less, particularly 10% by weight or less, based on the weight of water does not interfere with the reaction. Various problems, on the other hand, will arise in using the organic solvents in amounts exceeding 20% by weight based on the weight of water. For example, in the case of methanol, by-products are formed, resulting in a serious drop in the yield of HTCD. When ketones containing active hydrogen, for example, acetone is used, the conversion of TMP seriously drops. Also, in the case of carboxylic acids, for example, trifluoroacetic acid, and amines, for example, trimethylamine, hypohalogenous acid or salt thereof decomposes or TMP forms salts, undesirably lowering the conversion of TMP.

Preferred organic solvents as used herein include nitriles having from 1 to 4 carbon atoms, such as acetonitrile, propionitrile, and butyronitrile, carboxylic acid esters derived from carboxylic acids having from 1 to 6 carbon atoms and alcohols having from 1 to 6 carbon atoms, such as methyl acetate, ethyl acetate, n-propyl acetate, iso-propyl acetate, n-butyl acetate, iso-butyl acetate, tert-butyl acetate, methyl propionate, ethyl propionate, methyl butyrate, ethyl butyrate, cyclohexyl acetate, and methyl benzoate, ethers having from 2 to 8 carbon atoms, such as ethyl ether, n-butyl ether, isopropyl ether, tetrahydrofuran, 1,4-dioxane, and 1,2-dimethoxyethane, nitro compounds having from 1 to 6 carbon atoms, such as nitromethane, nitroethane, and nitrobenzene, amides having from 1 to 4 carbon atoms, such as dimethylformamide (DMF), dimethylacetamide (DMAC), and acetamide, nitrogen-containing heterocyclic compounds having from 4 to 7 carbon atoms, such as pyridine, picoline, lutidine, quinoline, and morpholine, aliphatic hydrocarbons having from 5 to 10 carbon atoms, alicyclic hydrocarbons having from 5 to 10 carbon atoms, and aromatic hydrocarbons having from 6 to 12 carbon atoms, such as n-pentane, n-hexane, n-heptane, n-octane, iso-octane, petroleum ether, petroleum benzine, ligroin, cyclohexane, benzene, toluene, xylene, ethylbenzene, solvent naphtha, and terpin oil, and their halogenated compounds, i.e., halogenated hydrocarbons obtained by halogenation of hydrocarbon, such as methylene chloride, chloroform, carbon tetrachloride, ethyl chloride, 1,1,1-trichloroethane, 1,1,2-trichloroethane, 1,1,2,2-tetrachloroethane, butyl chloride, amyl chloride, chlorobenzene, o-chlorobenzene, bromobenzene, and fluorotrichloromethane, carbon disulfide ($CS_2$), dimethylsulfoxide (DMSO), aliphatic carbonic acid esters having from 3 to 7 carbon atoms, such as diethyl carbonate, phosphoric acid esters having from 3 to 9 carbon atoms, such as triethyl phosphate, sulforane, and the like. Of these compounds, carboxylic acid esters, hydrocarbons, and halogenated hydrocarbons are particularly preferred in view of yields, and from industrial and economical viewpoints.

In general, the amount of the organic solvent to be used is not critical in the invention. The optimum amount of the organic solvent is determined by the concentration of TMP in the organic solvent and the ratio of water to organic solvent. When the concentration of TMP is high, the reaction rate tends to increase excessively, lowering the selectivity of HTCD. Thus, too high concentrations of TMP should be avoided. On the other hand, when the concentration of TMP is too low, a large quantity of energy is undesirably consumed in distilling away the solvent for the recovery of HTCD. Thus, the weight ratio of organic solvent to TMP is suitable to be 50:1 or less, preferably 10:1 or less and more preferably 2:1 or less. The ratio of water to organic solvent in the reaction system has great influences on the selectivity of HTCD; that is, if it is below a certain value, the selectivity of HTCD drops. Thus, the ratio of water to organic solvent is at least 2:1, preferably at least 4:1, and more preferably at least 10:1.

When the reaction rate is low, the reaction can be accelerated by adding various additives. For example, where organic solvents having very low solubility in water, such as petroleum ether, are used, a group of compounds generally known as surface active agents, phase transfer catalysts, or crown ethers can be added to increase the reaction rate.

In adding these surface active agents, phase transfer catalysts, and crown ethers, the amount of each compound being added is from 0.0001 to 10 parts by weight, preferably from 0.001 to 1 part by weight, and particularly preferably from 0.005 to 0.5 part by weight per part by weight of TMP.

In the reaction of the invention, the concentration of hydrogen ions, i.e., pH, greatly influences the conversion of TMP, the selectivity of HTCD, and the yield of HTCD. The pH range is preferably from 4 to 13.5 (from slightly acidic to slightly alkaline) and more preferably from 5 to 13, with the range of from 6 to 12.5 being most preferred. The adjustment of pH to the desired range can be carried out by various techniques, for example, by keeping the pH of hypohalogenous acid or salt thereof within a suitable range, adding caustic alkalis, e.g., NaOH or KOH, or by adding mineral acids, e.g., HCl or $H_2SO_4$, to the reaction system. By conducting the reaction while keeping the pH within the preferred range, a suitable selectivity can be attained, and the undesired decomposition of HTCD can be effectively prevented. Of course, it is effective to adjust each of the starting materials, TMP and hypohalogenous acid or salt thereof, within the above-described pH ranges prior to the reaction.

In connection with the reaction temperature, it is not necessary to heat because the reaction rate is usually sufficiently high even at room temperature. However, depending on reaction conditions, the reaction rate may be low. In this case, it is possible to increase the reaction rate by performing the reaction at temperatures higher than room temperature. When, however a high concentration solution or suspension of hypohalogenous acid or salt thereof and a high concentration solution of TMP are contacted, a large quantity of energy is generated, increasing the liquid temperature of the reaction system. In this case, it is preferred to keep the liquid at lower temperature by cooling. In general, as the reaction temperature is lowered, the selectivity tends to increase although the reaction rate drops. Thus, the reaction temperature is usually from 0° to 150° C., preferably from 0° to 100° C., and more particularly from 0° to 60° C., with the range of from 10° to 50° C. being particularly preferred.

The reaction in the process of the invention can be carried out in various manners, for example, by a method in which an aqueous solution or suspension of hypohalogenous acid or salt thereof is gradually added dropwise to a solution of TMP while stirring, by a method in which, contrarily, a solution of TMP is gradually added dropwise to an aqueous solution or suspension of hypohalogenous acid or salt thereof while stirring, and by a method of supplying hypohalogenous acid or salt thereof and TMP at the same time to cause them to react. In cases where the contact of HTCD formed with hypohalogenous acid or salt thereof may cause undesirable secondary reactions, various techniques can be employed to prevent such undesirable secondary reactions.

In accordance with a typical method in which the reaction is performed in the presence of organic solvent-containing aqueous medium, an aqueous solution or suspension hypohalogenous acid or its salt is added to the reaction medium, or vice versa.

In this method in which the reaction is carried out while adding an aqueous solution or suspension of hypohalogenous acid or salt thereof, of the above-described organic solvents to be used, those organic solvents are preferred which are not completely soluble in water, but have great affinity to water. In particular, carboxylic acid esters, or mixed solvents containing carboxylic acid esters are preferred. Preferred are carboxylic acid esters derived from carboxylic acids having from 1 to 7 carbon atoms and alcohols having from 1 to 5 carbon atoms. Examples of these carboxylic acid esters are ethyl acetate, n-propyl acetate, n-butyl acetate, methyl propionate, ethyl propionate, methyl butyrate, ethyl butyrate, cyclohexyl acetate, methyl benzoate, and the like. In preparing mixed solvents containing carboxylic acid esters, those solvents having low affinity to water can be used. Preferred examples are aliphatic hydrocarbons having from 5 to 10 carbon atoms, alicyclic hydrocarbons having from 5 to 10 carbon atoms, aromatic hydrocarbons having from 6 to 12 carbon atoms, and halogenated hydrocarbons obtained by halogenation of the hydrocarbons. The carboxylic acid ester content of these mixed solvents is preferably at least 10% by volume.

On the other hand, in the method in which the reaction is carried out while adding an organic solvent solution of TMP to an aqueous solution or suspension of hypohalogenous acid or salt thereof, it is preferred to employ organic solvents having low affinity to water in view of the selectivity of reaction. In particular, hydrocarbons and halogenated hydrocarbons as described above are preferred. Typical examples are aliphatic, alicyclic, and aromatic hydrocarbons, such as n-pentane, n-hexane, n-heptane, n-octane, isooctane, petroleum ether, petroleum benzine, ligroin, cyclohexane, benzene, toluene, xylene, ethylbenzene, solvent naphtha, and terpin oil, and halogenated hydrocarbons, such as methylene chloride, chloroform, and chlorobenzene.

In the method in which the reaction is carried out while adding an organic solvent solution of TMP to an aqueous solution or suspension of hypohalogenous acid or salt thereof, since organic solvents having low affinity to water are used, only a limited amount of organic solvent moves into the aqueous phase. This gives rise to the advantage that the loss of organic solvent in the recovery of the reaction product is small and, therefore, the quantity of energy required for the recovery of organic solvent can be reduced.

The process of the present invention can be also carried out by a continuous process in which hypohalogenous acid or salt thereof and TMP are reacted while feeding them concurrently. In the industrial practice, the continuous process is more suitable than the batch process. That is, this continuous process offers great advantages in that it is easier to control the reaction because the reaction equipment can be automated, and in that the number of operators can be reduced compared with the batch process.

This continuous process can be carried out in both an aqueous medium and an organic solvent-containing aqueous medium. For example, in using organic solvents having relatively great affinity to water, at least one reactor is employed, and it is preferred that at least two reactors are employed for increasing the conversion of TMP and the selectivity of HTCD. When two or more reactors are used, it is preferred that a solution of TMP dissolved in a predetermined amount of organic solvent is continuously introduced into the first reactor, and from 1/10 to ½ mole, preferably from 1/5 to ⅓ mole of a solution or suspension of hypohalogenous acid or salt thereof per mole of TMP is continuously introduced. The residence time of the reaction liquid in the first reactor is adjusted to from 0.1 to 60 minutes and preferably from 1 to 50 minutes. Then, the reaction liquid is withdrawn from the first reactor and sent to the second reactor. In the second reactor and the subsequent reactor or reactors, the solution or suspension of hypohalogenous acid or salt thereof is continuously fed in an amount of from ½ to 9/10 mole, preferably from ⅔ to 4/5 mole, per mole of TMP supplied to the first reactor, and the residence time is adjusted to from 0.1 to 60 minutes, preferably from 1 to 30 minutes.

When organic solvents having poor affinity to water are used, it is preferred that at least two reactors are employed. In the first reactor, a solution or suspension of hypohalogenous acid or salt thereof and TMP, the molar ratio of TMP to the hypohalogenous acid or salt thereof being from 1/5 to ½ and preferably from ¼ to ⅓, are continuously fed, and the residence time of the reaction liquid is adjusted to from 0.1 to 30 minutes and preferably from 1 to 20 minutes. The reaction liquid is continuously withdrawn from the first reactor and sent to the second reactor. In the second reactor and the subsequent reactor or reactors, TMP alone is usually fed in an amount of from ½ to 4/5 mole, preferably from ½ to ⅔ mole, per mole of the hypohalogenous acid or salt thereof supplied to the first reactor.

In performing the reaction in aqueous medium, there is usually used only one reactor. TMP is continuously introduced into the reactor in the form of powder, and a solution or suspension of hypohalogenous acid or salt thereof is also continuously introduced in an amount of from 0.5 to 2 moles, preferably from 0.8 to 1.3 moles per mole of TMP. The reaction liquid is withdrawn from the reactor so that the residence time is from 0.1 minute to 2.0 hours and preferably from 1 minute to 1.0 hour. If the reaction is not completed in the first reactor, the reaction liquid is continuously withdrawn from the first reactor and introduced into the second reactor where the reaction liquid is further reacted at a residence time of from 0.2 minute to 0.7 hour and preferably from 1 minute to 0.5 hour.

Although the above explanation has been made by reference to a cascade type continuous process, other tubular type reactors can be used to prevent secondary reactions. For example, a plug flow type reactor into which a TMP solution or solid TMP and a solution or suspension of hypohalogenous acid or salt thereof are introduced through its inlet by means of a pump or feeder can be used with much better results.

After the reaction is completed, HTCD formed is separated and recovered by the usual techniques. When organic solvents thoroughly soluble in water are used, there can be employed a process in which the water and/or organic solvents are first removed, for example, by distillation, and HTCD is then extracted with any suitable solvent and separated. When organic solvents having low solubility in water are used, an aqueous phase and an oil phase are separated from each other, the aqueous phase is repeatedly subjected to an extraction treatment using the same organic solvent to transfer the HTCD formed thereto, the thus-formed oil phase are combined together, and the organic solvent is distilled away for the separation and recovery of HTCD, and re-used.

When, on the other hand, no organic solvent is used, the oily product is separated as such, or the oily product is separated by solvent extraction and the solvent used is distilled away to recover HTCD.

The process of the invention permits high efficient preparation of HTCD from TMP. That is, in accordance with the process of the invention, HTCD which is a precursor for 2,3,5-trimethylhydroquinone, a starting material in the preparation of vitamin E, can be prepared by a simplified operation, safely and at high yields.

The present invention will hereinafter be explained in detail by reference to the following examples.

EXAMPLE 1

Water (40 milliliters) was placed in a 200-milliliter four-necked flask, and 2.00 grams of TMP was added and suspended therein. To the resulting mixture was added dropwise 16 milliliters of a 6% aqueous solution of sodium hypochlorite adjusted to pH 12.5 through a dropping funnel over a period of 15 minutes. After the addition was completed, stirring was continued for additional 10 minutes. After the reaction was completed, the reaction mixture was separated into two layers, and the product was present in the lower layer in an oily form. The pH of the aqueous layer was 11.3.

The reaction mixture was extracted three times with 100 milliliters of ethyl acetate. The ethyl acetate was distilled away from the extracted liquid to obtain 2.17 grams of a residue.

Analysis showed that the residue contained 1.45 grams of HTCD and 0.20 gram of TMP. That is, the conversion of TMP was 89.6%, and the yield of HTCD was 65.0%.

EXAMPLE 2

The procedure of Example 1 was repeated wherein the reaction temperature was changed as shown in Table 1. The results are shown in Table 1 below.

TABLE 1

| Run No. | Concentration of Sodium Hypochlorite (%) | Reaction Temperature (°C.) | Conversion of TMP (%) | Yield of HTCD (%) |
|---|---|---|---|---|
| 1 | 6 | 25 | 97.0 | 68.7 |
| 2 | 6 | 50 | 97.3 | 61.7 |
| 3 | 6 | 70 | 93.4 | 65.4 |

EXAMPLE 3

The procedure of Example 1 was repeated wherein the pH of the aqueous sodium hypochlorite solution was changed using 1 normal hydrochloric acid, as shown in Table 2. The results are shown in Table 2.

TABLE 2

| Run No. | pH of Sodium Hypochlorite Solution | Conversion of TMP (%) | Yield of HTCD (%) |
|---|---|---|---|
| 1 | 11.0 | 98.8 | 75.6 |
| 2 | 10.0 | 98.1 | 80.2 |
| 3 | 9.1 | 95.8 | 80.9 |
| 4 | 8.5 | 80.7 | 58.7 |

EXAMPLE 4

The procedure of Example 1 was repeated wherein the pH of the aqueous sodium hypochlorite solution was changed to 9.5, and the pH of the reaction system was adjusted to 4.0, 6.9, 9.2, 10.0 and 13.8 with Clark (phthalic acid-based buffer), Sørensen (phosphate buffer), Sørensen (borate buffer), Nenzel (carbonate buffer), and a 0.5% NaOH solution, respectively. The results are shown in Table 3 below.

TABLE 3

| Run No. | pH of Reaction System | Conversion of TMP (%) | Yield of HTCD (%) |
|---|---|---|---|
| 1 | 4.0 | 86.7 | 64.3 |
| 2 | 6.9 | 89.0 | 71.5 |
| 3 | 9.2 | 96.4 | 79.5 |
| 4 | 10.0 | 97.4 | 76.7 |
| 5 | 13.8 | 96.0 | 16.0 |

EXAMPLE 5

The procedure of Example 1 was repeated wherein the pH of the aqueous sodium hypochlorite solution was changed to 10.0, and the amount of water to be added to the reaction system was changed as shown in Table 4. The results are shown in Table 4 below.

TABLE 4

| Run No. | Amount of Water (milliliters) | Conversion of TMP (%) | Yield of HTCD (%) |
|---|---|---|---|
| 1 | 10 | 90.3 | 63.5 |
| 2 | 20 | 94.0 | 71.4 |
| 3 | 40 | 98.1 | 80.2 |
| 4 | 80 | 96.9 | 78.3 |

EXAMPLE 6

Water (40 milliliters) was placed in a 200-milliliter four-necked flask, and 2.00 grams of TMP was added and suspended therein. pH electrodes were placed in the flask so that the pH of the reaction mixture could be measured continuously. To the above-prepared mixture were added 16 milliliters of a 6% aqueous solution of sodium hypochlorite (pH 12.5) and further, 1 normal hydrochloric acid so as to maintain the pH of the reaction mixture within the range of from 8.5 to 9.5, through dropping funnels at room temperature (25° C.) over a period of 30 minutes. After the dropwise addition was completed, stirring was continued for additional 10 minutes. Thereafter, the same procedure as in Example 1 was performed. The results are as follows:

Conversion of TMP: 97.5%
Yield of HTCD: 80.0%

EXAMPLE 7

A solution of 2.00 grams of TMP dissolved in 25 milliliters of ethyl acetate, and 25 milliliters of water were placed in a 200-milliliter four-necked flask and stirred. To the resulting mixture was added dropwise 100 milliliters of a 1% aqueous solution of sodium hypochlorite adjusted to pH 12.5 through a dropping funnel over a period of 60 minutes. After the dropwise addition was completed, the mixture was further stirred for 30 minutes. The pH of the reaction mixture at the time of completion of the addition was 11.0.

After the reaction was completed, an organic phase and an aqueous phase were separated. The aqueous phase was extracted three times with 100 milliliters of ethyl acetate. The organic phase and the extracted liquid were combined together, and the ethyl acetate was distilled away by a rotary evaporator to obtain 2.35 grams of a residue.

Gas chromatographic analysis showed that the residue contained 2.11 grams of 4-hydroxy-2,4,6-trimethyl-cyclohexa-2,5-dien-1-one (HTCD), and that no unreacted TMP remained. In addition to HTCD, 0.07 gram of 3,5-dimethyl-4-hydroxybenzaldehyde and 0.05 gram of quinone dimer were obtained. That is, the conversion of TMP was 100%, and the yield of HTCD was 94.5%.

EXAMPLE 8

The procedure of Example 7 was repeated wherein various carboxylic acid esters were used in place of ethyl acetate. The results are shown in Table 5 below.

TABLE 5

| Run No. | Carboxylic Acid Ester | Conversion of TMP (%) | Yield of HTCD (%) |
|---|---|---|---|
| 1 | n-Propyl acetate | 99.4 | 93.4 |
| 2 | n-Butyl acetate | 99.0 | 87.2 |
| 3 | Amyl acetate | 98.4 | 92.0 |
| 4 | Methyl propionate | 99.3 | 93.8 |
| 5 | Ethyl propionate | 99.5 | 90.9 |
| 6 | iso-Amyl propionate | 97.9 | 77.6 |
| 7 | Methyl butyrate | 98.8 | 86.7 |
| 8 | Ethyl butyrate | 98.3 | 81.9 |
| 9 | Isopropyl acetate | 100 | 89.0 |
| 10 | Isoamyl acetate | 99.1 | 89.3 |
| 11 | Pentyl acetate | 95.2 | 78.2 |
| 12 | Fusel acetate | 100 | 84.3 |
| 13 | Amyl acetate | 100 | 89.5 |

EXAMPLE 9

The procedure of Example 7 was repeated wherein various organic solvents were used in place of ethyl acetate. The results are shown in Table 6 below.

TABLE 6

| Run No. | Organic Solvent | Conversion of TMP (%) | Yield of HTCD (%) |
|---|---|---|---|
| 1 | Benzene | 97.1 | 57.8 |
| 2 | Chlorobenzene | 96.3 | 71.7 |
| 3 | Carbon tetrachloride | 99.0 | 76.7 |
| 4 | Chloroform | 97.3 | 79.8 |
| 5 | Dichloromethane | 99.0 | 82.8 |
| 6 | Hexane | 97.2 | 70.0 |

EXAMPLE 10

A solution of 2.00 grams of TMP dissolved in 25 milliliters of benzene, and 25 milliliters of water were placed in a 100-milliliter four-necked flask and stirred. To the resulting mixture were added 0.50 gram of tetrabutylammonium hydrogensulfate (n-Bu$_4$NHSO$_4$) and 2.00 grams of bleaching powder, which were then stirred at room temperature for 30 minutes.

After the reaction was completed, an organic phase and an aqueous phase were separated. The aqueous phase was extracted three times with 100 milliliters of ethyl acetate. The organic phase and the extracted liquid were combined together, and the solvent was distilled away by a rotary evaporator to obtain 2.20 grams of a residue.

Analysis showed that the residue contained 1.17 grams of HTCD and 0.22 gram of TMP. That is, the conversion of TMP was 89.2%, and the yield of HTCD was 52.3%.

By comparison with the reaction in which tetrabutylammonium hydrogensulfate was not used (conversion: 42.0%; yield: 18.7%), it can be seen that the tetrabutylammonium hydrogensulfate has the reaction accelerating effect.

EXAMPLE 11

The procedure of Example 10 was repeated wherein 0.53 gram of dibenzo-18-crown-6 was used in place of tetrabutylammonium hydrogensulfate. There was obtained 2.19 grams of a residue.

By analysis of the residue, 0.82 gram of HTCD and 0.44 gram of TMP were detected. That is, the conversion of TMP was 77.7%, and the yield of HTCD was 36.8%.

EXAMPLE 12

The procedure of Example 7 was repeated wherein in place of ethyl acetate, a benzene/ethyl acetate mixed solvent (ethyl acetate: 16% by volume), a toluene/ethyl acetate mixed solvent (ethyl acetate: 32% by volume), or a hexane/ethyl acetate mixed solvent (ethyl acetate: 32% by volume) was used. The results are shown in Table 7 below.

TABLE 7

| Run No. | Mixed Solvent | Conversion of TMP (%) | Yield of HTCD (%) |
|---|---|---|---|
| 1 | Benzene/Ethyl acetate | 98.3 | 91.2 |
| 2 | Toluene/Ethyl acetate | 100 | 92.0 |
| 3 | Hexane/Ethyl acetate | 100 | 83.9 |

EXAMPLE 13

The procedure of Example 7 was repeated wherein the concentration of sodium hypochlorite (pH, 12.5) was changed to 2%, and the concentration of TMP in ethyl acetate was changed as shown in Table 8. The results are shown in Table 8.

TABLE 8

| Run No. | Concentration of TMP (mole/liter) | Conversion of TMP (%) | Yield of HTCD (%) |
|---|---|---|---|
| 1 | 0.59 | 100 | 82.4 |
| 2 | 1.18 | 100 | 74.7 |

EXAMPLE 14

A 1% aqueous solution of sodium hypochlorite (96 milliliters) adjusted to pH 12.5 was placed in a 200-milliliter four-necked flask and stirred. To this aqueous solution was added dropwise a solution of 2.00 grams of TMP dissolved in 25 milliliters of benzene at room temperature (25° C.) through a dropping funnel over a period of 1 hour. After the dropwise addition was completed, stirring was continued for additional 30 minutes. The pH of the reaction mixture at the time of completion of the addition was 11.2.

After the reaction was completed, an organic phase and an aqueous phase were separated. The aqueous phase was extracted three times with 100 milliliters of ethyl acetate. The organic phase and the extracted liquid were combined together, and the ethyl acetate was distilled away by a rotary evaporator to obtain 2.22 grams of a residue.

By analysis of the residue, 1.89 grams of HTCD and 0.19 gram of TMP were detected. That is, the conversion of TMP was 90.6%, and the yield of HTCD was 83.9%.

The reaction was performed in the same manner as above except that the temperature was set at 0° C. In this case, the conversion of TMP was 100%, and the yield of HTCD was 86.6%

EXAMPLE 15

Two vessel type reactors, each being provided with a stirrer, were used to perform a continuous flow reaction.

The first and second reactors were charged with 130 grams of water and 250 grams of water, respectively. To the first reactor, 20 grams per hour (g/hr) of fully ground TMP powder was fed continuously through a feeder, and at the same time, 240 grams per hour (g/hr) of a 2% sodium hypochlorite solution adjusted to pH 10.0 with concentrated hydrochloric acid was fed continuously. The reaction mixture was well stirred so that it did not separate into two layers, and it was continuously withdrawn from the first reactor at a rate of 260 grams per hour (g/hr) and sent to the second reactor. To the second reactor, 240 grams per hour (g/hr) of a 2% sodium hypochlorite solution was supplied, and the resulting mixture was vigorously stirred so that it did not separate into two layers as in the first reactor. The reaction mixture was withdrawn from the second reactor at a rate of 500 grams per hour (g/hr). The thus-withdrawn mixture was then analyzed. In both the first and second reactors, the residence time of the reaction mixture was 30 minutes, and the reaction was carried out for 8 hours.

At predetermined intervals, about 100 milliliters of the reaction mixture was taken out, and the products and unreacted starting materials were extracted with ethyl acetate and determined by gas chromatography.

About three hours after the introduction of the starting materials, the reaction reached a nearly stationary state, and the pH of the reaction mixture was from 8.8 to 9.1.

The results are shown as Run No. 1 in Table 9.

For comparison, the same reaction as above was performed using one reactor. In this case, the selectivity of HTCD was low. The results are also shown as Run No. 2 in Table 9.

TABLE 9

| Run No. | Reaction Time (hours) | Conversion of TMP (%) | Yield of HTCD (%) | Remarks |
|---|---|---|---|---|
| 1 | 3 | 97.0 | 81.0 | |
| | 4 | 97.0 | 78.2 | |
| | 5 | 97.1 | 81.3 | |
| | 6 | 97.4 | 78.2 | |
| | 7 | 97.5 | 78.8 | |
| | 8 | 97.5 | 81.0 | |
| 2 | 7 | 97.5 | 71.0 | one reactor |

Comparative Example

Two grams of TMP and 25 milliliters of methanol were placed in a 200-milliliter four-necked flask, and stirred at room temperature. To this methanol solution of TMP was added dropwise 17 milliliters of 6% aqueous solution of sodium hypochlorite through a dropping funnel over a period of 40 minutes. After the dropwise addition was completed, stirring was further continued for 1 hour. During the reaction, crystals insoluble in methanol precipitated.

After the reaction was completed, the crystals insoluble in methanol were filtered off. The portion soluble in methanol was analyzed by gas chromatography. HTCD was not detected, 4-methoxy-2,4,6-trimethylcyclohexa-2,5-diene-1-one was detected, the yield being 5%, and the starting material, TMP, was not detected. Infrared absorption analysis of the portion insoluble in methanol indicated that it was a polyphenylene ether type polymeric material.

What is claimed is:

1. A process for producing 4-hydroxy-2,4,6-trimethylcyclohexa-2,5-diene-1-one which comprises 2,4,6-trimethylphenol with reacting hypohalogenous acid or salt thereof in an aqueous medium or mixed medium of water and at least one organic solvent selected from the group consisting of nitriles having from 1 to 4 carbon atoms, carboxylic acid esters derived from carboxylic acids having from 1 to 6 carbon atoms and alcohols having from 1 to 6 carbon atoms, ethers having from 2 to 8 carbon atoms, nitro compounds having from 1 to 6 carbon atoms, amides having from 1 to 4 carbon atoms, nitrogen-containing heterocyclic compounds having from 4 to 7 carbon atoms, aliphatic hydrocarbons having from 5 to 10 carbon atoms, alicyclic hydrocarbons having from 5 to 10 carbon atoms, aromatic hydrocarbons having from 6 to 12 carbon atoms, halogenated hydrocarbons obtained by halogenation of said hydrocarbons, carbon disulfide, dimethylsulfoxide, aliphatic carbonic acid esters having from 3 to 7 carbon atoms, phosphoric acid esters having from 3 to 9 carbon atoms, and sulforane under the condition that the weight ratio of water to 2,4,6-trimethylphenol is at least 10:1.

2. A process as claimed in claim 1, wherein the hypohalogenous acid is hypochloric acid.

3. A process as claimed in claim 1, wherein the hypohalogenous acid salt is sodium hypochlorite or bleaching powder.

4. A process as claimed in claim 1, wherein the amount of the hypohalogenous acid or salt thereof used is from 0.1 to 10 moles per mole of 2,4,6-trimethylphenol.

5. A process as claimed in claim 1, wherein the amount of the hypohalogenous acid or salt thereof used is from 0.5 to 2 moles per mole of 2,4,6-trimethylphenol.

6. A process as claimed in claim 1, wherein the amount of the hypohalogenous acid or salt thereof used is from 0.8 to 1.3 moles per mole of 2,4,6-trimethylphenol.

7. A process as claimed in claim 1, wherein the hypohalogenous acid or salt thereof is added to the reaction system in the form of aqueous solution or aqueous suspension.

8. A process as claimed in claim 7, wherein the concentration of the hypohalogenous acid or salt thereof in the aqueous solution or the aqueous suspension is from 0.1 to 15% by weight.

9. A process as claimed in claim 7, wherein the concentration of the hypohalogenous acid or salt thereof in the aqueous solution or the aqueous suspension is from 0.5 to 8% by weight.

10. A process as claimed in claim 1, wherein the pH of the reaction mixture is maintained at from 4 to 13.5.

11. A process as claimed in claim 1, wherein the pH of the reaction mixture is maintained at from 5 to 13.

12. A process as claimed in claim 1, wherein the reaction temperature is from 0° to 150° C.

13. A process as claimed in claim 1, wherein the reaction temperature is from 0° to 60° C.

14. A process as claimed in claim 1, wherein the reaction temperature is from 10° to 50° C.

15. A process as claimed in claim 1, wherein the reaction is carried out in an aqueous medium.

16. A process as claimed in claim 1, wherein the reaction is carried out in a mixed medium of water and one or more organic solvents selected from the group consisting of carboxylic acid esters derived from carboxylic acids having from 1 to 6 carbon atoms and alcohols having from 1 to 6 carbon atoms, aliphatic hydrocarbons having from 5 to 10 carbon atoms, alicyclic hydrocarbons having from 5 to 10 carbon atoms, aromatic hydrocarbons having from 6 to 12 carbon atoms, and halogenated hydrocarbons obtained by halogenation of said hydrocarbons.

17. A process as claimed in claim 1 or 16, wherein said reaction is carried out in said mixed medium and the weight ratio of water to the organic solvent in the mixed medium is at least 2:1.

18. A process as claimed in claim 1 or 16, wherein said reaction is carried out in said mixed medium and the weight ratio of the organic solvent to 2,4,6-trimethylphenol is at least 50:1.

19. A process as claimed in claim 1 or 16, wherein the reaction is carried out by adding an aqueous solution or suspension of hypohalogenous acid or salt thereof to an organic solvent solution of 2,4,6-trimethylphenol.

20. A process as claimed in claim 19, wherein the organic solvent is a carboxylic acid ester derived from a carboxylic acid having from 1 to 6 carbon atoms and an alcohol having from 1 to 6 carbon atoms.

21. A process as claimed in claim 1 or 16, wherein the reaction is carried out by adding an organic solvent solution of 2,4,6-trimethylphenol to an aqueous solution or suspension of hypohalogenous acid or salt thereof.

22. A process as claimed in claim 21, wherein the organic solvent is one or more compounds selected from the group consisting of aliphatic hydrocarbons having from 5 to 10 carbon atoms, alicyclic hydrocarbons having from 5 to 10 carbon atoms, aromatic hydrocarbons having from 6 to 12 carbon atoms, and halogenated hydrocarbons obtained by halogenation of said hydrocarbons.

23. A process as claimed in claim 1 or 16, wherein at least one additive selected from the group consisting of surface active agents and phase transfer catalysts is added.

24. A process as claimed in claim 1, wherein the reaction is performed continuously while feeding both the hypohalogenous acid or salt thereof and 2,4,6-trimethylphenol.

25. A process as claimed in claim 24, wherein the reaction is carried out in an aqueous medium.

26. A process as claimed in claim 24, wherein the reaction is carried out in a mixed medium of water and one or more organic solvents selected from the group consisting of carboxylic acid esters derived from carboxylic acids having from 1 to 6 carbon atoms and alcohols having from 1 to 6 carbon atoms, aliphatic hydrocarbons having from 5 to 10 carbon atoms, alicyclic hydrocarbons having from 5 to 10 carbon atoms, aromatic hydrocarbons having from 6 to 12 carbon atoms, and halogenated hydrocarbons obtained by halogenation of said hydrocarbons.

27. A process as claimed in claim 24, wherein at least one additive selected from the group consisting of surface active agents and phase transfer catalysts is added.

28. A process as claimed in claim 24, comprising continuously reacting 2,4,6-trimethylphenol with the aqueous solution or suspension of hypohalogenous acid or salt thereof in at least two reactors by the use of an organic solvent having great affinity to water, wherein the organic solvent solution of 2,4,6-trimethylphenol and the aqueous solution or suspension of hypohalogenous acid or salt thereof are continuously fed to the first reactor so that the molar ratio of the hypohalogenous acid or salt thereof to 2,4,6-trimethylphenol is from 1/10 to ½.

29. A process as claimed in claim 28, wherein the organic solvent is a carboxylic acid ester derived from a carboxylic acid having from 1 to 6 carbon atoms and an alcohol having from 1 to 6 carbon atoms.

30. A process as claimed in claim 24, comprising continuously reacting 2,4,6-trimethylphenol with the aqueous solution or suspension of hypohalogenous acid or salt thereof in at least two reactors by the use of an organic solvent having low affinity to water, wherein the organic solvent solution of 2,4,6-trimethylphenol and the aqueous solution or suspension of hypohalogenous acid or salt thereof are continuously fed to the first reactor so that the molar ratio of the 2,4,6-trimethylphenol to the hypohalogenous acid or salt thereof is from 1/5 to ½.

31. A process as claimed in claim 30, wherein the organic solvent is one or more compounds selected from the group consisting of aliphatic hydrocarbons having from 5 to 10 carbon atoms, alicyclic hydrocarbons having from 5 to 10 carbon atoms, aromatic hydrocarbons having from 6 to 12 carbon atoms, and halogenated hydrocarbons obtained by halogenation of said hydrocarbons.

32. A process as claimed in claim 24, wherein the reaction is performed in a tubular type reactor.

33. A process as claimed in claim 1, further comprising:
conducting the reaction in said mixed medium at a temperature of from 0° to 150° C., wherein the molar ratio of hypohalogenous acid or salt thereof to 2,4,6-trimethylphenol is from 0.1 to 10, and the weight ratio of water to the organic solvent in the mixed medium is at least 2:1.

34. A process as claimed in claim 33, further comprising:
conducting said reaction at a temperature of 0° to 60° C. and maintaining the pH of the reaction mixture at a pH of 4 to 13.5, wherein the hypohalogenous acid or salt thereof is an aqueous solution or aqueous suspension of hypochloric acid or sodim hypochlorite, the molar ratio of hypochloric acid or sodium hypochlorite to 2,4,6-trimethylphenol is from 0.5 to 2, the concentration of hypochloric acid or sodium hypochlorite in the aqueous solution or the aqueous suspension is from 0.1 to 15% by weight, the weight ratio of water to 2,4,6-trimethylphenol is at least 20, and the weight ratio of water to the organic solvent in the mixed medium is at least 5.

35. A process as claimed in claim 34, wherein the salt of hypohalogenous acid is sodium hypochlorite, the organic solvent is a carboxylic acid ester derived from carboxylic acids having from 1 to 6 carbon atoms and alcohols having from 1 to 6 carbon atoms, the reaction temperature is from 0° to 50° C., the molar ratio of sodium hypochlorite to 2,4,6-trimethylphenol is from 0.8 to 1.3, the concentration of sodium hypochlorite in the aqueous solution or the aqueous suspension is from 0.5 to 8% by weight, the pH of the reaction mixture is maintained at from 5 to 13, the weight ratio of water to 2,4,6-trimethylphenol is at least 25, and the weight ratio of water to the organic solvent in the mixed medium is at least 10.

* * * * *

UNITED STATES PATENT AND TRADEMARK OFFICE
CERTIFICATE OF CORRECTION

PATENT NO. : 4,477,682
DATED : October 16, 1984
INVENTOR(S) : Tetsuo TOMITA, et al It is certified that error appears in the above-identified patent and that said Letters Patent is hereby corrected as shown below:

Column 1, line 29, change "bendesired" to --been desired--;

Column 5, line 36, after "halogenation of" insert --a--;

Column 14, line 5 (claim 1), after "comprises" insert --reacting--;

Column 14, line 6 (claim 1), change "reacting" to --a--;

Column 16, line 44 (claim 34), change "sodim" to --sodium--.

Signed and Sealed this

Fourteenth Day of January 1986

[SEAL]

Attest:

DONALD J. QUIGG

Attesting Officer     Commissioner of Patents and Trademarks